(12) United States Patent
Oda et al.

(10) Patent No.: US 9,321,046 B2
(45) Date of Patent: Apr. 26, 2016

(54) RECOVERY METHOD AND RECYCLING METHOD FOR BORON TRIFLUORIDE COMPLEX

(71) Applicant: IDEMITSU KOSAN CO., LTD., Chiyoda-ku (JP)

(72) Inventors: Sumihiro Oda, Chiba (JP); Masashi Machida, Chiba (JP); Hiroki Sekiguchi, Chiba (JP); Yukio Yoshida, Chiba (JP); Toshiyuki Tsubouchi, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

(21) Appl. No.: 14/382,492

(22) PCT Filed: Mar. 1, 2013

(86) PCT No.: PCT/JP2013/055731
§ 371 (c)(1),
(2) Date: Sep. 2, 2014

(87) PCT Pub. No.: WO2013/129662
PCT Pub. Date: Sep. 6, 2013

(65) Prior Publication Data
US 2015/0133691 A1    May 14, 2015

(30) Foreign Application Priority Data
Mar. 2, 2012  (JP) .................... 2012-047436

(51) Int. Cl.
*C07F 5/02*   (2006.01)
*B01J 38/56*  (2006.01)
*B01J 31/40*  (2006.01)
*C07C 41/38*  (2006.01)
*C07C 41/42*  (2006.01)
*B01J 31/22*  (2006.01)
*C07C 2/04*   (2006.01)

(52) U.S. Cl.
CPC .............. *B01J 38/56* (2013.01); *B01J 31/2208* (2013.01); *B01J 31/40* (2013.01); *C07C 2/04* (2013.01); *C07C 41/38* (2013.01); *C07C 41/42* (2013.01); *C07F 5/022* (2013.01); *B01J 2231/20* (2013.01); *C07C 2102/42* (2013.01); *Y02P 20/584* (2015.11)

(58) Field of Classification Search
USPC ........................................................ 568/1, 6
See application file for complete search history.

(56) References Cited

U.S. PATENT DOCUMENTS 2,941,939 A  *  6/1960  Shiah ........................ 208/241
2005/0272597 A1 * 12/2005  Hironaka et al. .......... 502/150

FOREIGN PATENT DOCUMENTS

| JP | 2 45429 | 2/1990 |
|---|---|---|
| JP | 2000 109313 | 4/2000 |
| JP | 2000 128522 | 5/2000 |
| JP | 2000 135402 | 5/2000 |
| JP | 2000 135403 | 5/2000 |
| JP | 2001 104805 | 4/2001 |
| JP | 2004 141819 | 5/2004 |
| JP | 2004 195360 | 7/2004 |

OTHER PUBLICATIONS

International Search Report Issued Apr. 16, 2013 in PCT/JP13/055731 Filed Mar. 1, 2013.

* cited by examiner

*Primary Examiner* — Fereydoun G Sajjadi
*Assistant Examiner* — Pancham Bakshi
(74) *Attorney, Agent, or Firm* — Oblon, McClelland, Maier & Neustadt, L.L.P.

(57) ABSTRACT

In a reaction in which a boron trifluoride complex is used as a catalyst, the expensive and harmful boron trifluoride complex is separated from a reaction mixture containing the boron trifluoride complex by separating the boron trifluoride complex present in the reaction mixture by using a saturated hydrocarbon-based solvent.

13 Claims, No Drawings

RECOVERY METHOD AND RECYCLING METHOD FOR BORON TRIFLUORIDE COMPLEX

CROSS REFERENCE TO RELATED APPLICATIONS

The present application is a 35 U.S.C. §371 national stage patent application of International patent application PCT/JP2013/055731, filed on Mar. 1, 2013, published as WO/2013/129662 on Sep. 6, 2013, the text of which is incorporated by reference, and claims the benefit of the filing date of Japanese application no. 2012-047436, filed on Mar. 2, 2012, the text of which is also incorporated by reference.

TECHNICAL FIELD

The present invention relates to processes for the recovery and recycling of a boron trifluoride complex, and more particularly, it relates to processes for the recovery of a boron trifluoride complex and reusing of the boron trifluoride complex recovered, wherein the boron trifluoride complex is used as a catalyst in a process for producing compounds by alkylation, condensation reaction of olefins, oligomerization reaction, polymerization reaction, condensation reaction and isomerization reaction, and in a process for producing petroleum resins, chroman, and indene-resins.

BACKGROUND ART

Boron trifluoride and a boron trifluoride complex constituted of boron trifluoride and a complexing agent (ligand) are well known as a so-called Friedel-Crafts catalyst, and the boron trifluoride complex has an excellent catalyst performance of suppressing side reactions and promoting only main reactions effectively as compared with $AlCl_3$, $FeCl_3$, sulfuric acid and the like. Therefore, various boron trifluoride complexes are industrially used widely as a catalyst in various chemical reactions such as alkylation, isomerization, polymerization, dimerization, condensation, addition, decomposition, dehydration, etc.

Main industrial use of the boron trifluoride or boron trifluoride complex includes, for example, a catalyst in producing ethyl benzene by gas phase alkylation from ethylene and benzene. The boron trifluoride or boron trifluoride complex is also used as a catalyst in the process for producing alkyl benzenes used for synthetic detergents or antioxidants by liquid phase alkylation reaction of an olefin and an aromatic compound.

Furthermore, the boron trifluoride or boron trifluoride complex is also used as a polymerization catalyst in producing petroleum resins and chroman-indene resins which are widely used in the fields such as adhesives and printing ink. When the boron trifluoride or boron trifluoride complex is used as the polymerization catalyst, it is possible to attain effects such as less deterioration in quality of a product and less corrosion of an equipment used. As mentioned above, the boron trifluoride or boron trifluoride complex provides a catalyst that can be used in various applications as a catalyst for production of various products in chemical industries.

The boron trifluoride complex constituted of boron trifluoride and a complexing agent (ligand) is used, depending on the reaction as intended, in the form of a complex in which various compounds are coordinated to boron trifluoride at an appropriate ratio. The boron trifluoride complex acts as a catalyst in the reaction as intended. It is general that the boron trifluoride complex is deactivated after stopping the reaction as intended to separate the boron trifluoride complex from the resulting reaction mixture. In order to separate the boron trifluoride complex from the reaction mixture, there are usually adopted a method of washing the reaction mixture with water after adding water to the reaction mixture to deactivate the boron trifluoride complex therein, a method of washing the reaction mixture with water after neutralizing the reaction mixture solution by a basic aqueous solution of ammonia, sodium hydroxide, lime or the like.

However, in the above methods, a waste water containing a hydrate of boron trifluoride or a neutralized product of boron trifluoride in a high concentration is discharged. Therefore, in recent years, there is a demand for suitable measures to be taken for removal of the waste water containing fluorides or boron in consideration of the problem of environmental pollution. In particular, since it is difficult to remove boron easily by a current technology for waste-water treatment, and since it is costly to remove boron completely, there is a demand for removal of boron at low costs. Furthermore, since boron trifluoride is expensive, there is a demand for recovery and reuse of the removed boron trifluoride or boron trifluoride complex.

However, for example, in the condensation reaction of olefins using the boron trifluoride complex as a catalyst, the boron trifluoride complex is almost dissolved in the reaction mixture or forms an emulsion. Hence, even if the reaction mixture is allowed to stand, it is difficult to completely separate the reaction mixture and the boron trifluoride complex catalyst from each other. Therefore, the boron trifluoride complex is removed from the reaction mixture by washing the reaction mixture with water or the basic aqueous solution. However, if water or the basic aqueous solution is added to the boron trifluoride complex, the boron trifluoride catalyst forms a water complex such as $BF_3(H_2O)_n$, or a boron trifluoride salt, and cannot be repeatedly used as a catalyst as it is. Also, there is known a method of separating a catalyst liquid layer from the reaction mixture using a complex of $BF_3$ with phosphoric acid, acetic acid or phenol (for example, refer to Patent Document 1). However, the above reaction proceeds only slowly unless the catalyst concentration is 10% or more. Moreover, since the catalyst acts as a Broensted acid, side reactions such as isomerization tend to occur, and consequently the aforementioned separation method cannot be adopted particularly for a condensation dimerization reaction of olefins.

Conventionally, there is known a method for the recovery of boron trifluoride or a boron trifluoride complex, wherein the reaction mixture solution containing the boron trifluoride or boron trifluoride complex is contacted with calcium fluoride ($CaF_2$) at a temperature of 200° C. or lower, and the resulting calcium tetrafluoroborate ($Ca(BF_4)_2$) is heated at a temperature between 100° C. and 600° C., to obtain the boron trifluoride to be recovered and calcium fluoride (for example, refer to Patent Document 2).

Similarly, there is known a method for the recovery of boron trifluoride by contacting a fluoride such as lithium fluoride, strontium fluoride and barium fluoride with the reaction mixture solution containing the boron trifluoride or boron trifluoride complex to produce a tetrafluoroborate and heating the tetrafluoroborate at a temperature between 100° C. and 600° C. (for example, refer to Patent Document 3, Patent Document 4 and Patent Document 5).

However, in the reaction using the boron trifluoride or boron trifluoride complex as a catalyst, it is necessary to react at a low temperature below room temperature in many cases. Moreover, when the temperature is raised to about 100° C. after stopping the reaction, at which the tetrafluoroborate is synthesized advantageously, a side reaction tends to occur, which results in decrease in the yield of the reaction product as aimed or deterioration in quality thereof. The tetrafluoroboric acid is hardly formed below room temperature. In addition, decomposition reaction by heating at high temperature is not desirable from the viewpoint of energy saving.

Moreover, there is a problem that, when the reaction mixture solution containing the boron trifluoride or boron trifluoride complex is viscous, much time and effort are required in order to separate borates such as calcium tetrafluoroborate from the reaction mixture.

There is also known a method for the recovery of the boron trifluoride or boron trifluoride complex, wherein the boron trifluoride or boron trifluoride complex is precipitated and separated from a nonconducting fluid by applying d.c. voltage and/or a.c. voltage to the nonconducting fluid in which boron trifluoride is dispersed and/or dissolved, and then the boron trifluoride or boron trifluoride complex thus separated is heated (for example, refer to Patent Document 6).

However, in the recovery method, it is necessary to use an electrical facility capable of continuously applying a voltage of several hundreds of volts from an external power supply for a time period of 30 minutes or longer after stopping the reaction. Since a side reaction tends to occur owing to the application of voltage, a process for stopping the reaction is required. There is also a problem that the boron trifluoride or boron trifluoride complex dissolved in the reaction mixture is not always separated completely by the application of voltage.

Furthermore, there is disclosed a method of recovering boron trifluoride or a boron trifluoride complex using a hydrofluorocarbon compound, etc., and reusing the recovered boron trifluoride or boron trifluoride complex (for example, refer to Patent Documents 7 and 8). In the method, there can be attained a good recovery rate of the boron trifluoride or boron trifluoride complex. However, there remains such a problem that the hydrofluorocarbon used is expensive. In addition, since organic substances are dissolved in the hydrofluorocarbon, it is necessary to additionally conduct the step of removing the organic substances from the hydrofluorocarbon.

CITATION LIST

Patent Literature

Patent Document 1: JP 02-45429A
Patent Document 2: JP 2000-109313A
Patent Document 3: JP 2000-128522A
Patent Document 4: JP 2000-135402A
Patent Document 5: JP 2000-135403A
Patent Document 6: JP 2001-104805A
Patent Document 7: JP 2004-195360A
Patent Document 8: JP 2004-141819A

SUMMARY OF THE INVENTION

Problem to be Solved by the Invention

The prevent invention has been made in view of the above problems encountered in the conventional art. An object of the present invention is to provide a method of recovering a boron trifluoride complex in which the expensive and harmful boron trifluoride complex is separated from a reaction mixture containing the boron trifluoride complex in a facilitated manner, and a method of reusing the thus recovered boron trifluoride complex in the reaction.

Means for Solving the Problem

As a result of extensive and intensive researches for solving the above problems, the present inventors have found that a specific hydrocarbon-based solvent is substantially incapable of dissolving a boron trifluoride complex present in a reaction mixture, but is capable of dissolving a reaction product and a raw material of the reaction product which are present in the reaction mixture. The present invention has been accomplished on the basis of this finding.

That is, the present invention provides the following aspects.

1. A method of recovering a boron trifluoride complex used as a catalyst in a reaction, including the step of separating the boron trifluoride complex present in a reaction mixture obtained in the reaction from the reaction mixture by using a saturated hydrocarbon-based solvent.
2. The method of recovering a boron trifluoride complex as described in the above aspect 1, wherein the saturated hydrocarbon-based solvent comprises a linear or branched saturated hydrocarbon having 5 to 16 carbon atoms.
3. The method of recovering a boron trifluoride complex as described in the above aspect 1 or 2, wherein the saturated hydrocarbon-based solvent comprises at least one material selected from the group consisting of linear or branched pentane, hexane, heptane, octane, nonane and decane; and cyclohexane, a petroleum ether, naphtha and light naphtha, or a mixture of any two or more of these materials.
4. The method of recovering a boron trifluoride complex as described in any one of the above aspects 1 to 3, wherein the saturated hydrocarbon-based solvent is added to a reaction vessel together with a reaction raw material and the boron trifluoride complex before initiation of the reaction, and after stopping the reaction, the boron trifluoride complex present in the reaction mixture is separated therefrom.
5. The method of recovering a boron trifluoride complex as described in any one of the above aspects 1 to 3, wherein the saturated hydrocarbon-based solvent is added to a reaction vessel after stopping the reaction to separate the boron trifluoride complex present in the reaction mixture therefrom.
6. The method of recovering a boron trifluoride complex as described in any one of the above aspects 1 to 5, wherein after separating a liquid layer containing the boron trifluoride complex from the reaction mixture, the thus separated liquid layer is subjected to distillation to increase a purity of the boron trifluoride complex therein.
7. The method of recovering a boron trifluoride complex as described in any one of the above aspects 1 to 6, wherein a complexing agent that forms a complex with boron trifluoride in the boron trifluoride complex comprises a polar compound.
8. The method of recovering a boron trifluoride complex as described in the above aspect 7, wherein the complexing agent is at least one compound selected from the group consisting of alcohols, ethers, phenols, amines, ketones, aldehydes, esters, acid anhydrides and acids.
9. The method of recovering a boron trifluoride complex as described in any one of the above aspects 1 to 8, wherein the boron trifluoride complex comprises a boron trifluoride ether complex.
10. The method of recovering a boron trifluoride complex as described in any one of the above aspects 1 to 9, wherein the reaction in which the boron trifluoride complex is used as a catalyst is selected from the group consisting of a dimerization reaction, an oligomerization reaction, a condensation reaction and a polymerization reaction of an olefin.

11. A method of recycling a catalyst, including the step of reusing the boron trifluoride complex recovered by the method as described in any one of the above aspects 1 to 10 as a catalyst in the reaction.

Effect of the Invention

According to the present invention, it is possible to provide a method of separating and recovering an expensive and harmful boron trifluoride complex from a reaction mixture containing the boron trifluoride complex in a facilitated manner, and also provide a method of reusing the thus recovered boron trifluoride complex in the reaction.

Preferred Embodiments for Carrying out the Invention

The present invention relates to a method of recovering a boron trifluoride complex used as a catalyst in a reaction, including the step of separating the boron trifluoride complex present in a reaction mixture obtained in the reaction from the reaction mixture by using a saturated hydrocarbon-based solvent, and a method of reusing the thus recovered boron trifluoride complex in the reaction.

Examples of the reaction in which the boron trifluoride complex of the present invention is used as a catalyst include a dimerization reaction, an oligomerization reaction, a polymerization reaction and a copolymerization reaction of olefins, as well as various chemical reactions including an alkylation reaction such as a Friedel-Crafts alkylation reaction, a condensation reaction, an isomerization reaction, a decomposition reaction, a dehydration reaction and the like.

Incidentally, the dimerization reaction and oligomerization reaction of olefins include a reaction of two different kinds of olefins and an oligomerization reaction of two or more kinds of olefins.

Examples of the olefins used as the raw material in the above reactions include α-olefin compounds, cyclic olefin compounds, and aromatic olefin compounds.

Specific examples of the α-olefin compounds include 1-butene, 1-hexene, 1-octene, 1-decene, 1-dodecene, isobutene, diisobutylene, and dimers such as a 1-butene dimer, a 1-hexene dimer, a 1-octene dimer and a 1-dodecene dimer.

Specific examples of the cyclic olefin compounds include cyclohexene, cyclooctene, norbornene, methyl bicyclo[2.2.1]heptenes, dimethyl bicyclo[2.2.1]heptenes, camphene, β-pinene, limonene, β-caryophyllene, longifolene, valencene and guaiene.

Specific examples of the aromatic olefin compounds include styrene and α-methyl styrene.

Examples of the boron trifluoride complex used as a catalyst in the present invention include a boron trifluoride ethyl ether complex, a boron trifluoride methyl ether complex, a boron trifluoride ethyl methyl ether complex, a boron trifluoride butyl ether complex, a boron trifluoride phenol complex, a boron trifluoride alkylamine complex, a boron trifluoride ammonia complex, a boron trifluoride piperidine complex, a boron trifluoride triethanolamine complex, boron trifluoride alcohol complexes, boron trifluoride ketone complexes, boron trifluoride aldehyde complexes, boron trifluoride ester complexes, boron trifluoride acid anhydride complexes and boron trifluoride acid complexes.

In the present invention, a liquid layer containing the boron trifluoride complex or the boron trifluoride complex as a single substance is separated from the reaction mixture containing a reaction product, a raw material and the boron trifluoride complex as a catalyst by using a saturated hydrocarbon-based solvent. The saturated hydrocarbon used as the solvent may be either a chain saturated hydrocarbon or a cyclic saturated hydrocarbon. The chain saturated hydrocarbon may be in the form of either a straight-chain saturated hydrocarbon or a branched-chain saturated hydrocarbon. The saturated hydrocarbon-based solvent is likely to dissolve the reaction product and the raw material contained in the reaction mixture, but hardly dissolves the boron trifluoride complex contained in the reaction mixture. As a result, the saturated hydrocarbon-based solvent can provide a facilitated procedure of separation of the boron trifluoride complex in the subsequent stage. Also, the saturated hydrocarbon-based solvent has no malodor and a good safety.

In the present invention, as the saturated hydrocarbon-based solvent, there are preferably used saturated hydrocarbons having 5 to 16 carbon atoms. Saturated hydrocarbon-based solvents having 4 or less carbon atoms are kept in a gas state at a normal temperature and a normal pressure, and therefore tend to be difficult to handle under these conditions. On the other hand, saturated hydrocarbons having 17 or more carbon atoms are kept in a solid state at a normal temperature and a normal pressure, and therefore also tend to be difficult to handle under these conditions.

Specific examples of the saturated hydrocarbon-based solvent include linear or branched pentane, hexane, heptane, n-octane, isooctane, 2-ethylhexane, nonane, isononane and decane, and cyclohexane. Other specific examples of the saturated hydrocarbon-based solvent include industrial products containing as a main component, linear or branched pentane, hexane, heptane, isooctane, 2-ethylhexane, nonane, isononane or decane, or cyclohexane. Still other specific examples of the saturated hydrocarbon-based solvent include petroleum ethers (having 5 and 6 carbon atoms) and naphtha or soft naphtha (having 5 to 12 carbon atoms).

In the present invention, these saturated hydrocarbon-based solvents may be used alone or in the form of a mixture of any two or more thereof.

Of these saturated hydrocarbon-based solvents, in view of a good availability, preferred are linear saturated hydrocarbons having 5 to 9 carbon atoms, and in view of a high safety in addition to the good availability, more preferred are saturated hydrocarbon-based solvents having 6 to 7 carbon atoms, and especially preferred is heptane.

In the present invention, the recovery of the boron trifluoride complex is preferably conducted by separating the boron trifluoride complex present in the reaction mixture therefrom by the following method A or method B.

(Method A)

In the reaction using the boron trifluoride complex as a catalyst, before initiation of the reaction, the above saturated hydrocarbon-based solvent is charged together with the reaction raw material and the boron trifluoride complex into a reaction vessel, and after stopping the reaction, the boron trifluoride complex present in the resulting reaction mixture is separated from the reaction mixture.

(Method B)

In the reaction using the boron trifluoride complex as a catalyst, after stopping the reaction, the above saturated hydrocarbon-based solvent is added to the reaction vessel to separate the boron trifluoride complex present in the resulting reaction mixture therefrom.

That is, the saturated hydrocarbon-based solvent may be added to the reaction vessel either before initiation of the reaction or after stopping the reaction. The saturated hydrocarbon-based solvent causes no side reactions such as alkylation reactions, and condensation and oligomerization of olefins, and therefore may be added even before initiation of the reaction.

By conducting any of the above methods A or B, the reaction mixture can be separated into an upper liquid layer containing the reaction product and the raw material and a lower liquid layer containing the boron trifluoride complex. The thus separated lower liquid layer solution may be reused as the catalyst. Further, the lower liquid layer solution may also be subjected to distillation to enhance a purity of the boron trifluoride complex contained in the lower liquid layer solution. The distillation of the lower liquid layer solution may be carried out by conventionally known methods.

In the present invention, the saturated hydrocarbon-based solvent as an extraction solvent for separating the boron trifluoride complex is preferably used in an amount of from 10 to 500 parts by mass, and more preferably from 20 to 200 parts by mass, on the basis of 100 parts by mass of the reaction raw material, when added before initiation of the reaction. On the other hand, when added after stopping the reaction, the saturated hydrocarbon-based solvent is preferably used in an amount of from 10 to 500 parts by mass, and more preferably from 20 to 200 parts by mass, on the basis of 100 parts by mass of the reaction mixture obtained after stopping the reaction. In the case where the extraction solvent is added after stopping the reaction, a whole amount of the extraction solvent may be added to the reaction mixture at one time, or may be intermittently added in two or more split parts to the reaction mixture. In view of a good separation efficiency, the extraction solvent is preferably intermittently added in a plurality of split parts to the reaction mixture.

The temperature used upon separating the boron trifluoride complex with the saturated hydrocarbon-based solvent is 40° C. or lower, and preferably 25° C. or lower. The standing time upon allowing the reaction mixture to stand for separating the boron trifluoride complex therefrom with the saturated hydrocarbon-based solvent is preferably 30 min or longer, and more preferably from about 30 min to about 120 min.

In the method of recycling the boron trifluoride complex according to the present invention, the lower liquid layer solution containing the boron trifluoride complex separated and recovered by the above method is used in a process for producing compounds by alkylation reactions, condensation reactions of olefins, oligomerization reactions, polymerization reactions, condensation reactions and isomerization reactions, or in a process for producing petroleum resins, chroman, and indene resins.

As described above, according to the present invention, by using the saturated hydrocarbon-based solvent, it is possible to separate the boron trifluoride complex from the reaction mixture containing the reaction product, the raw material and the boron trifluoride complex in a facilitated manner. This is because the saturated hydrocarbon-based solvent has such a peculiar property that it is capable of dissolving the reaction product and the raw material contained in the reaction mixture, but hardly dissolves the boron trifluoride complex contained in the reaction mixture.

The mechanism of the above separation is considered to be that the saturated hydrocarbon-based solvent dissolves the reaction product and the raw material contained in the reaction mixture to form an interface between the resulting solution and the boron trifluoride complex.

As described above, according to the present invention, it is possible to separate the boron trifluoride complex that is conventionally hardly disposed of by a waste treatment can be separated in a facilitated manner. In addition, the separated solution can be used as a reaction catalyst, so that it is possible to reduce an amount of wastes.

EXAMPLES

The present invention will be described in more detail below with reference to the following Examples. However, these Examples are only illustrative and not intended to limit the invention thereto.

Example 1

(1) Separation of Boron Trifluoride Complex

A mixture containing 2-methylene-3-methyl bicyclo[2.2.1]heptane and 3-methylene-2-methyl bicyclo[2.2.1] both produced as raw materials of synthetic lubricating oils in a total amount of 55% by mass, and containing 2,3-dimethyl bicyclo[2.2.1]hept-2-ene in an amount of 30% by mass and a structural isomer thereof, was prepared as a raw material, and subjected to the following dimerization reaction.

A 100 L-capacity reaction vessel was charged with 6 kg of hexane, 600 g of a boron trifluoride diethyl ether complex and 30 kg of the above raw material, and the contents of the reaction vessel were subjected to dimerization reaction at 0° C. for 12 h while stirring with a mechanical stirrer. After stopping the reaction, the resulting reaction mixture was allowed to stand and separated into two liquid layers. Thereafter, 258 g of the black separated solution (lower liquid layer) containing the boron trifluoride diethyl ether complex was obtained. As a result, it was confirmed that a recovery rate of the separated solution containing the boron trifluoride diethyl ether complex was 43%.

(2) Evaluation of Activity of Catalyst Recovered

In order to evaluate a catalytic activity of the boron trifluoride diethyl ether complex recovered, 200 g of the above raw material was reacted with 4.0 g of the separated solution containing the boron trifluoride diethyl ether complex recovered, at 0° C. As a result, it was confirmed that the reaction proceeded at substantially the same reaction rate as that attained in the reaction using a virgin boron trifluoride diethyl ether complex, namely, the boron trifluoride diethyl ether complex recovered had substantially the same activity as that of a fresh boron trifluoride diethyl ether complex.

Example 2

The separated solution containing the boron trifluoride diethyl ether complex recovered in Example 1 was subjected to distillation under a reduced pressure of 20 kPa in a temperature range of from 84 to 90° C. As a result, a colorless transparent boron trifluoride diethyl ether complex was obtained with a recovery rate of 72%. The thus obtained boron trifluoride diethyl ether complex had substantially the same activity as that of a virgin catalyst.

Comparative Example 1

The dimerization reaction was carried out in the same manner as in Example 1 except that 6 kg of hexane was not used. Although the resulting reaction mixture was allowed to stand for 40 min after stopping the reaction, the reaction mixture was not separated into two liquid layers, and therefore it was not possible to recover a separated solution containing the boron trifluoride diethyl ether complex.

Comparative Example 2

The reaction was carried out in the same manner as in Example 1 except that 6 kg of toluene was used in place of 6 kg of hexane. Although the resulting reaction mixture was allowed to stand for 40 min after stopping the reaction, the reaction mixture was not separated into two liquid layers, and therefore it was not possible to recover a separated solution containing the boron trifluoride diethyl ether complex.

INDUSTRIAL APPLICABILITY

In accordance with the present invention, it is possible to separate an expensive and harmful boron trifluoride complex from a reaction mixture containing a reaction product, a raw material and the boron trifluoride complex in a facilitated manner. In addition, since the above separated solution can be used as a reaction catalyst, it is possible to reduce an amount of wastes. Therefore, the present invention can be effectively used as technologies for saving of energy and environmental protection.

The invention claimed is:

1. A method of recovering a boron trifluoride complex used as a catalyst in a reaction, comprising separating the boron trifluoride complex present in a reaction mixture obtained in the reaction from the reaction mixture by contacting the reaction mixture with a saturated hydrocarbon-based solvent followed by allowing the reaction mixture to stand for at least 30 minutes after stopping the reaction.

2. The method of claim 1, wherein the saturated hydrocarbon-based solvent comprises a linear or branched saturated hydrocarbon having 5 to 16 carbon atoms.

3. The method of claim 1, wherein the saturated hydrocarbon-based solvent comprises at least one material selected from the group consisting of a pentane, a hexane, a heptane, an octane, a nonane, a decane, cyclohexane, a petroleum ether, naphtha and light naphtha, wherein the pentane, hexane, heptane, octane and nonane each independently may be linear or branched.

4. The method of claim 1, wherein the saturated hydrocarbon-based solvent is added to a reaction vessel together with a reaction raw material and the boron trifluoride complex before initiation of the reaction, and after stopping the reaction, the boron trifluoride complex present in the reaction mixture is separated therefrom.

5. The method of claim 1, wherein the saturated hydrocarbon-based solvent is added to a reaction vessel after stopping the reaction to separate the boron trifluoride complex present in the reaction mixture therefrom.

6. The method of claim 1, further comprising separating a liquid layer comprising the boron trifluoride complex from the reaction mixture to form a separated liquid layer, and distilling the separated liquid layer to increase a purity of the boron trifluoride complex therein.

7. The method of claim 1, wherein the boron trifluoride complex comprises a polar compound as the complexing agent, and the complexing agent forms a complex with boron trifluoride in the boron trifluoride complex.

8. The method of claim 7, wherein the complexing agent comprises at least one compound selected from the group consisting of an alcohol, an ether, a phenol, an amine, a ketone, an aldehyde, an ester, an acid anhydride and an acid.

9. The method of claim 1, wherein the boron trifluoride complex comprises a boron trifluoride ether complex.

10. The method of claim 1, wherein the reaction in which the boron trifluoride complex is used as a catalyst is selected from the group consisting of a dimerization reaction, an oligomerization reaction, a condensation reaction and a polymerization reaction of an olefin.

11. A method of recycling a boron trifluoride complex, comprising reusing the boron trifluoride complex recovered by the method of claim 1 as a catalyst in a reaction.

12. The method of claim 1, wherein the saturated hydrocarbon-based solvent comprises a linear saturated hydrocarbon having 5 to 16 carbon atoms.

13. The method of claim 1, wherein the saturated hydrocarbon-based solvent comprises a branched saturated hydrocarbon having 5 to 16 carbon atoms.

* * * * *